(12) United States Patent
Vanmoor

(10) Patent No.: US 6,525,097 B1
(45) Date of Patent: Feb. 25, 2003

(54) METHOD OF TREATING A CANCEROUS CONDITION BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,632

(22) Filed: Nov. 21, 2000

Related U.S. Application Data

(60) Provisional application No. 60/174,860, filed on Jan. 7, 2000.

(51) Int. Cl.⁷ .............................................. A61K 31/195
(52) U.S. Cl. ................. 514/562; 514/550; 514/547
(58) Field of Search .............................. 514/562, 550, 514/547

(56) References Cited

U.S. PATENT DOCUMENTS

| | | | |
|---|---|---|---|
| 5,208,039 A | * 5/1993 | Poupon et al. | 424/490 |
| 5,430,064 A | * 7/1995 | Hirsch et al. | 514/554 |
| 5,576,351 A | * 11/1996 | Yoshimura et al. | 514/565 |
| 5,626,831 A | * 5/1997 | Moerkerken | 424/9.2 |
| 5,856,310 A | * 1/1999 | Hamilton et al. | 514/19 |
| 6,017,962 A | * 1/2000 | Schold et al. | 515/562 |
| 6,090,414 A | * 7/2000 | Passwater et al. | 424/702 |

OTHER PUBLICATIONS

Lu et al, Nutrition & Cancer, vol. 38(1), pp. 123–130, 2000.*
Saito et al, Chemical Abstracts, vol. 106, #201768n, 1987.*
Novo–Med, Chemical Abstracts, vol. 105, #102610c, 1986.*

* cited by examiner

*Primary Examiner*—James H. Reamer

(57) ABSTRACT

There is disclosed a method of treating a cancerous condition in a person in need of such treatment, which comprises enhancing the effectiveness of the person's immune system by the administration to such person of at least one aliphatic sulfur compound, preferably a sulfur-containing amino-acid derivative having the formula (I)

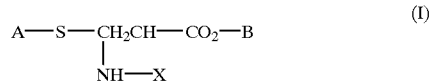

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

20 Claims, No Drawings

METHOD OF TREATING A CANCEROUS CONDITION BY ENHANCING THE EFFECTIVENESS OF THE HUMAN IMMUNE SYSTEM

CROSS-REFERENCES TO RELATED APPLICATIONS

This application claims the benefit of U.S. Provisional Application Ser. No. 60/174,860 filed Jan. 7, 2000.

BACKGROUND OF THE INVENTION

1. Field of the Invention

This invention relates to a method of treating a person suffering from a cancerous condition with an agent that enhances the effectiveness of the human immune system to minimize the effects of the cancerous condition.

2. Description of the Related Art

As is well known, cancerous conditions are characterized by the uncontrolled growth of tissues commonly known as tumors. Traditional attempts to mitigate the unfavorable effects of these have included surgical removal of tumors, administration of drugs that result in diminution of tumors, treatment with ionizing radiation to kill tumors, and all the possible combinations of these. The MERCK MANUAL, 16$^{th}$ edition, published 1992, at pages 1287 to 1292, which portion is here incorporated by reference, contains a table titled "Five Year Disease-free Survival Rates for Cancers Treated with Combined Therapies" listing the effectiveness in percent of various combination treatments against particular cancers at various stages. The table shows for only one out of 18 types of cancer a five year survival rate as high as 90%, and the subsequent discussion confirms that known therapies are limited in their effectiveness and accompanied by well known harmful side effects of each. There clearly remains a need for new approaches to finding and applying more effective and also less aggressive therapies.

As is also well known, the search for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in US patent no. as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

For evident reasons, however, this method is not applicable to the study and relief of cancerous conditions.

Yoshimura et al U.S. Pat. No. 5,576,351 disclosed treatment of an impaired human immune response by the administration of arginine or ornithine or mixtures thereof to humans suffering from impaired immune response or at risk of suffering impaired immune response. While it is stated that impaired immune response can be a secondary effect of such conditions as trauma or a debilitating disease such as cancer or infection with HIV virus, among others, there is no disclosure that any benefit in mitigating or relieving the effects of such conditions is obtained from administration of arginine or ornithine.

SUMMARY OF THE INVENTION

In accordance with this invention, there is provided a method of treating a cancerous condition in a person in need thereof, which comprises the administration to such person of at least one aliphatic sulfur compound. The effectiveness of the aliphatic sulfur compound according to the invention is believed to accompany enhancement of the effectiveness of the person's immune system.

The aliphatic sulfur compound preferably includes a sulfur-methylene moiety such as

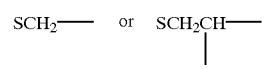

More preferably, the aliphatic sulfur compound also includes a carboxyl group, as in

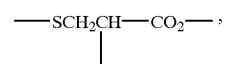

Still more preferably, the aliphatic sulfur compound is a sulfur-containing amino-acid derivative of an ethyl sulfide having the formula (I)

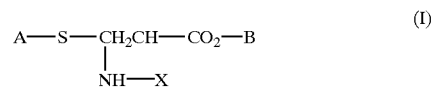

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

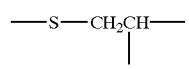

is believed to be responsible for the beneficial activity observed while the attached groups A, —NHX, and —$CO_2B$ assist in delivering the compound to the site within the human organism where the beneficial activity is exerted.

In one preferred embodiment, A is hydrogen.

In a further preferred embodiment, A, B, and X are not simultaneously hydrogen.

particularly suitable illustrative derivatives having the formula given above are tabulated by showing the assignments of A, B, and X in the above formula:

| Compound | A | B | X |
|---|---|---|---|
| 1 | —CH$_2$CO$_2$H | H | H |
| 2 | H | H | COCH$_3$ |
| 3 | H | CH$_3$ | H.HCl |
| 4 | H | C$_2$H$_5$ | H.HCl |
| 5 | H | H | H |
| 6 | H | H | H.HCl |

The present invention is based on the recognition that enhancing the effectiveness of the immune system in a person can be beneficial in augmenting the person's innate ability augmenting the person's innate ability to resist the initiation of the process that leads to a cancer condition as well as to slow down, arrest, and even reverse that process. As a result, the incidence of pain is diminished, and the quality of life is improved.

In increasing the effectiveness of the human immune system according to this invention, mega-nutrient doses of 2 to 20 grams of a compound or compounds of formula (I) can be administered from one to five times daily until monitoring shows sufficient improvement in the user's condition to permit reduction in dose level and ultimately cessation of the treatment. Such doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

One type of cancer condition that lends itself well to monitoring in simple ways without the need for hospitalization or the use of complex equipment is cancer of the prostate in the human male. It develops slowly over many years and is not considered highly life threatening. Yet even in its early stages it manifests itself in the well known enlargement of the prostate gland that results in pressure on the bladder and consequently a need for the victim to urinate much more frequently than a person without this condition, thus signaling a need to determine by appropriate test whether a cancer condition exists.

EXAMPLE 1

A group of male volunteers recorded for six weeks the number of times a night that they were awakened with the need to urinate. Those who woke up three or more times a night in more than 28 nights were then given multiple daily doses of 15–20 grams of a composition including several compounds of formula (I) and continued to record the number of times a night that they were awakened with the need to urinate.

Over time, there were volunteers whose awakening at night with the need to urinate diminished from three or more times a night to twice, once, and even none at all in at least two thirds of the nights in a subsequent trial period.

EXAMPLE 2

A male with prostate enlargement diagnosed as a cancerous condition started a regimen of taking 10 grams of composition as in Example 1 with each meal for a total of 40 grams daily. He felt relief after a few weeks; after two months of this regimen the prostate was found to have shrunk to normal size, and after 4 months of this regimen cancer was no longer found to be present.

EXAMPLE 3

A 19 year old female with three cysts on her ovaries took 20 grams of composition as in Example 1 daily; after 4 weeks of treatment the cysts had disappeared.

EXAMPLE 4

A 23 year old female with uterine cancer and endometrosis saw the cancer disappear after eight weeks of daily intake of 40 grams of composition as in Example 1.

What is claimed is:

1. A method of treating a cancerous condition in a person in need of such treatment, which comprises the administration to such person of at least one sulfur-containing amino-acid derivative having the formula (I)

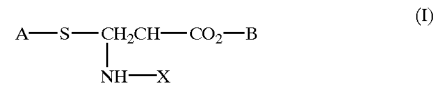

in which A is hydrogen or a carboxymetbylene —CH$_2$CO$_2$H group, B is hydrogen on an alkyl group having 1 to 3 carbon atoms, and X is an acyl group —CO—R in which R is an alkyl group having 1 to 3 carbon atoms, or a pharmaceutically acceptable salt of such compound.

2. The method of claim 1, wherein said amino-acid derivative is administered orally with food.

3. The method of claim 1, wherein said cancerous condition is cancer of the prostate gland.

4. The method of claim 1, wherein said amino-acid derivative is administered by injection into the bloodstream.

5. The method of claim 1, wherein said amino-acid derivative is administered by rectal suppository.

6. The method of claim 1, wherein said amino-acid derivative is administered in one to five daily doses of 2 to 20 grams each.

7. The method of claim 1, wherein the total of said amino-acid derivative administered daily is in the range of 20 to 50 grams.

8. The method of claim 1, wherein said amino-acid derivative is the compound of formula (I) in which A is H, B is H, and X is COCH$_3$.

9. The method of claim 1, wherein said person experiences relief from the effects of said condition.

10. The method of claim 1 wherein after treatment said condition is not detectable.

11. A method of treating a cancerous condition in a person in need of such treatment, which comprises enhancement of the person's immune system by the administration to such person of at least one sulfur-containing amino-acid derivative having the formula (I)

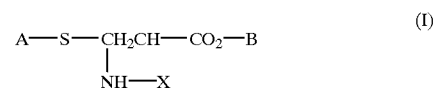

in which A is hydrogen or a carboxymethylene —CH$_2$CO$_2$H group, B is hydrogen or an alkyl group having 1 to 3 carton atoms, and X is hydrogen, or an acyl group —CO—R in where R is an alkyl group having 1 to 3 carbon atoms, or a pharmaceutically acceptable salt of such compound.

12. The method of claim 11, wherein said amino-acid derivative is administered orally with food.

13. The method of claim 11, wherein said cancerous condition is cancer of the prostate gland.

14. The method of claim 11, wherein said amino-acid derivative is administered by injection into the bloodstream.

15. The method of claim 11, wherein said amino-acid derivative is administered by rectal suppository.

16. The method of claim 11, wherein said amino-acid derivative is administered in one to five daily doses of 2 to 20 grams each.

17. The method of claim 11, wherein the total of said amino-acid derivative administered daily is in the range of 20 to 50 grams.

18. The method of claim 11, wherein said amino-acid derivative is the compound of formula (I) in which A is H, B is H, and X is $COCH_3$.

19. The method of claim 11, wherein said person experiences relief from the effect of said condition.

20. The method of claim 11, wherein after treatment said condition is not detectable.

* * * * *